US00PP28349P3

(12) United States Plant Patent
Hofmann

(10) Patent No.: US PP28,349 P3
(45) Date of Patent: Aug. 29, 2017

(54) ***MANDEVILLA* PLANT NAMED 'INMANSTAPI'**

(50) Latin Name: *Mandevilla sanderi*
Varietal Denomination: INMANSTAPI

(71) Applicant: INNOVAPLANT ZIERPFLANZEN GmbH & Co. KG, Gensingen (DE)

(72) Inventor: Birgit Hofmann, Rudesheim am Rhein (DE)

(73) Assignee: Innovaplant Zierpflanzen GmbH & Co. KG, Gensingen (DE)

( * ) Notice: Subject to any disclaimer, the term of this patent is extended or adjusted under 35 U.S.C. 154(b) by 33 days.

(21) Appl. No.: 14/998,347

(22) Filed: Jan. 4, 2016

(65) Prior Publication Data

US 2017/0196139 P1 Jul. 6, 2017

(51) Int. Cl.
*A01H 5/02* (2006.01)

(52) U.S. Cl.
USPC ..... Plt./232

(58) Field of Classification Search
USPC ..... Plt./232
See application file for complete search history.

*Primary Examiner* — Keith Robinson
(74) *Attorney, Agent, or Firm* — C. A. Whealy

(57) ABSTRACT

A new and distinct cultivar of *Mandevilla* plant named 'INMANSTAPI', characterized by its relatively compact plant habit; moderately vigorous growth habit; freely branching habit; relatively small glossy dark green-colored leaves; early and freely flowering habit; and relatively small flowers that are red purple in color with a light pink- colored central star pattern.

2 Drawing Sheets

Botanical designation: *Mandevilla sanderi.*
Cultivar denomination: 'INMANSTAPI'.

BACKGROUND OF THE INVENTION

The present invention relates to a new and distinct cultivar of *Mandevilla* plant, botanically known as *Mandevilla sanderi* and hereinafter referred to by the name 'INMANSTAPI'.

The new *Mandevilla* plant is a product of a planned breeding program conducted by the Inventor in Johannesburg, South Africa and Heidesheim, Germany. The objective of the breeding program is to create new compact and freely branching *Mandevilla* plants that flower early and freely and have unique and attractive flowers.

The new *Mandevilla* plant originated from a cross-pollination conducted by the Inventor in Johannesburg, South Africa in November, 2010 of a proprietary selection of *Mandevilla sanderi* identified as code number D09-1000-2, not patented, as the female, or seed parent with a proprietary selection of *Mandevilla sanderi* identified as code number D09-1000-6, not patented, as the male, or pollen, parent. The new *Mandevilla* plant was discovered and selected by the Inventor as a single flowering plant from within the progeny of the stated cross-pollination in a controlled greenhouse environment in Heidesheim, Germany in June, 2012.

Asexual reproduction of the new *Mandevilla* plant by cuttings in a controlled greenhouse environment in Heidesheim, Germany, since July, 2012 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INMANSTAPI'. These characteristics in combination distinguish 'INMANSTAPI' as a new and distinct *Mandevilla* plant:

1. Relatively compact plant habit.
2. Moderately vigorous growth habit.
3. Freely branching habit.
4. Relatively small glossy dark green-colored leaves.
5. Early and freely flowering habit.
6. Relatively small flowers that are red purple in color with a light pink-colored central star pattern.

Plants of the new *Mandevilla* can be compared to plants of the female parent selection. Plants of the new *Mandevilla* differ primarily from plants of the female parent selection in the following characteristics:

1. Plants of the new *Mandevilla* are more freely branching than plants of the female parent selection.
2. Plants of the new *Mandevilla* flower earlier than plants of the female parent selection.
3. Plants of the new *Mandevilla* have slightly larger flowers than plants of the female parent selection.
4. Plants of the new *Mandevilla* and the female parent selection differ in flower color as plants of the female parent selection have lighter-colored flowers with a less distinct central star pattern.

Plants of the new *Mandevilla* can be compared to plants of the male parent selection. Plants of the new *Mandevilla* differ primarily from plants of the male parent selection in the following characteristics:

1. Plants of the new *Mandevilla* are more freely branching than plants of the male parent selection.

2. Plants of the new *Mandevilla* flower earlier than plants of the male parent selection.
3. Plants of the new *Mandevilla* have slightly larger flowers than plants of the male parent selection.
4. Plants of the new *Mandevilla* and the male parent selection differ in flower color as plants of the male parent selection have dark red-colored flowers with a less distinct central star pattern.

Plants of the new *Mandevilla* can be compared to plants of *Mandevilla sanderi* 'Rio Pink', not patented. In side-by-side comparisons conducted in Heidesheim, Germany, plants of the new *Mandevilla* differed primarily from plants 'Rio Pink' in the following characteristics:

1. Plants of the new *Mandevilla* were more compact than plants of 'Rio Pink'.
2. Plants of the new *Mandevilla* had smaller leaves than plants of 'Rio Pink'.
3. Plants of the new *Mandevilla* had smaller flowers than plants of 'Rio Pink'.
4. Flowers of plants of the new *Mandevilla* had a distinct central star pattern whereas flowers of plants of 'Rio Pink' did not have a distinct central star pattern.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'INMANSTAPI' grown in a container.

The photograph on the second sheet is a close-up view of a typical flower of 'INMANSTAPI'.

DETAILED BOTANICAL DESCRIPTION

The aforementioned photographs and following observations, measurements and values describe plants grown during the late spring and early summer in 9.5-cm containers in a polyethylene-covered greenhouse in Almeria, Spain and under cultural practices typical of *Mandevilla* commercial production. During the production of the plants, day temperatures ranged from 20° C. to 35° C. and night temperatures ranged from 20° C. to 25° C. Plants were 15 weeks old when the photographs and description were taken. In the following description, color references are made to The Royal Horticultural Society Colour Chart, 2007 Edition, except where general terms of ordinary dictionary significance are used.

Botanical classification: *Mandevilla sanderi* 'INMANSTAPI'.

Parentage:

*Female, or seed, parent*.—Proprietary selection of *Mandevilla sanderi* identified as code number D09-1000-2.

*Male, or pollen, parent*.—Proprietary selection of *Mandevilla sanderi* identified as code number D09-1000-6.

Propagation:

*Type*.—By vegetative cuttings.

*Time to initiate roots, summer*.—About three weeks at temperatures ranging from 20° C. to 35° C.

*Time to initiate roots, winter*.—About three weeks at temperatures ranging from 20° C. to 25° C.

*Time to produce a rooted young plant, summer*.—About 25 to 30 days at temperatures ranging from 20° C. to 35° C.

*Time to produce a rooted young plant, winter*.—About 25 to 30 days at temperatures ranging from 20° C. to 25° C.

*Root description*.—Thick, fleshy; typically white in color, actual color of the roots is dependent on substrate composition, water quality, fertilizers, substrate temperature and physiological age of roots.

*Rooting habit*.—Low branching; medium density.

Plant description:

*Plant and growth habit*.—Relatively compact and upright plant habit; moderately vigorous growth habit.

*Plant height*.—About 21.8 cm.

*Plant diameter (spread)*.—About 21.6 cm.

*Lateral branch description*.—Branching habit: Freely branching habit with about four lateral branches developing per plant; pinching enhances lateral branch development. Length: About 16.9 cm. Diameter: About 2.5 mm. Internode length: About 2.9 cm. Strength: Strong. Texture and luster: Smooth, glabrous; moderately glossy. Color: Close to 143C.

Leaf description:

*Arrangement*.—Opposite, simple.

*Length*.—About 6.7 cm.

*Width*.—About 3.4 cm.

*Shape*.—Obovate to oblong.

*Apex*.—Short apiculate.

*Base*.—Rounded.

*Margin*.—Entire; slightly undulate.

*Texture and luster, upper and lower surfaces*.—Smooth, glabrous; glossy.

*Venation pattern*.—Pinnate.

*Color*.—Developing leaves, upper surface: Darker than between N137A and 147A. Developing leaves, lower surface: Close to 146A. Full expanded leaves, upper surface: Darker than between 139A and 147A; venation, close to 138A. Fully expanded leaves, lower surface: Close to between 144A and 146B; venation, close to 145A to 145B.

*Petiole length*.—About 1.1 cm.

*Petiole diameter*.—About 2 mm.

*Petiole texture, upper and lower surfaces*.—Smooth, glabrous.

*Petiole color, upper and lower surfaces*.—Close to 144B.

Flower description:

*Flower type and flowering habit*.—Single salverform flowers arranged in axillary cymes; flowers star-shaped and face mostly outwardly; freely flowering habit with about six flowers developing per inflorescence and about 100 flowers developing per plant during the flowering season.

*Natural flowering season*.—Plants flower continuously from early summer into the autumn in Spain.

*Flower longevity on the plant*.—About seven days; flowers not persistent.

*Fragrance*.—Faint; acidic-sweet and pleasant.

*Inflorescence height*.—About 11.9 cm.

*Inflorescence diameter*.—About 8.7 cm.

*Flower buds*.—Length: About 6.1 cm. Diameter: About 1 cm. Shape: Narrowly obovate to oblanceolate. Color: Close to 53C; towards the base, close to 150D.

*Flowers*.—Appearance: Flared trumpet, corolla fused and five-parted. Diameter: About 6.9 cm. Depth (length): About 7.7 cm.

*Corolla*.—Quantity and arrangement: Five petals arranged in a single whorl; lower portion of the petals are fused into a tube. Petal length: About 8.3 cm; fused portion, about 5.3 cm. Petal width: About 3.1 cm. Petal shape and appearance: Roughly spatulate. Petal apex: Non-symmetrically acute. Petal margin: Entire; irregularly undulate. Petal texture and luster, upper surface: Smooth, glabrous; moderately velvety; matte. Petal texture and luster, lower surface: Smooth, glabrous; slightly glossy. Throat and tube texture: Smooth, glabrous. Color: Petal, when opening, upper surface: Close to N57B; towards the apex, close to N57A; central star pattern, close to 62C to 62D; throat, close to 12A to 12C; at the base of the throat, close to N144D. Petal, when opening, lower surface: Close to 58B to 58D; white central band, close to N155B; tube, close to 150D; at the base of the tube, close to N144D. Petal, fully opened, upper surface: Close to N57B; towards the apex, close to N57A; central star pattern, close to 62D; throat, close to 12A to 12C; at the base of the throat, close to N144D; with development, main color becoming closer to N57C. Petal, fully opened, lower surface: Close to 58B to 58D; white central band, close to N155B; tube, close to 150D; at the base of the tube, close to N144D.

*Corona*.—Quantity and arrangement: Five sepals arranged in a single whorl. Sepal length: About 8 mm. Sepal width: About 2 mm. Sepal shape: Lanceolate. Sepal apex: Narrowly acuminate. Sepal base: Roughly truncate. Sepal margin: Entire. Sepal texture and luster, upper and lower surfaces: Smooth, glabrous; matte. Sepal color: Immature, upper and lower surfaces: Close to 145C; towards the base, close to 145A. Mature, upper and lower surfaces: Close to 145B; towards the base, close to 145A.

*Peduncles*.—Length: About 6.1 cm. Diameter: About 2 mm. Texture: Smooth, glabrous. Aspect: About 30° from lateral branch axis. Strength: Strong. Color: Close to 143A to 143B.

*Pedicels*.—Length: About 1.6 cm. Diameter: About 2 mm. Texture: Smooth, glabrous. Aspect: About 20° from peduncle axis. Strength: Strong. Color: Close to 145A.

*Reproductive organs*.—Stamens: Quantity and arrangement: Typically five; basifixed; anthers connivent. Filament length: About 1 mm. Anther shape: Narrowly oblong. Anther length: About 9 mm. Anther color: Close to 160B. Pollen amount: None observed. Pistils: Quantity: Typically one. Pistil length: About 2.9 cm. Style length: About 2.5 cm. Style color: Close to 150C to 150D. Stigma shape: Sagittate. Stigma color: Close to 150C. Ovary color: Close to 144A.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate high temperatures of about 40° C. and to be hardy to USDA Hardiness Zone 9.

It is claimed:

1. A new and distinct *Mandevilla* plant named 'INMANSTAPI' as illustrated and described.

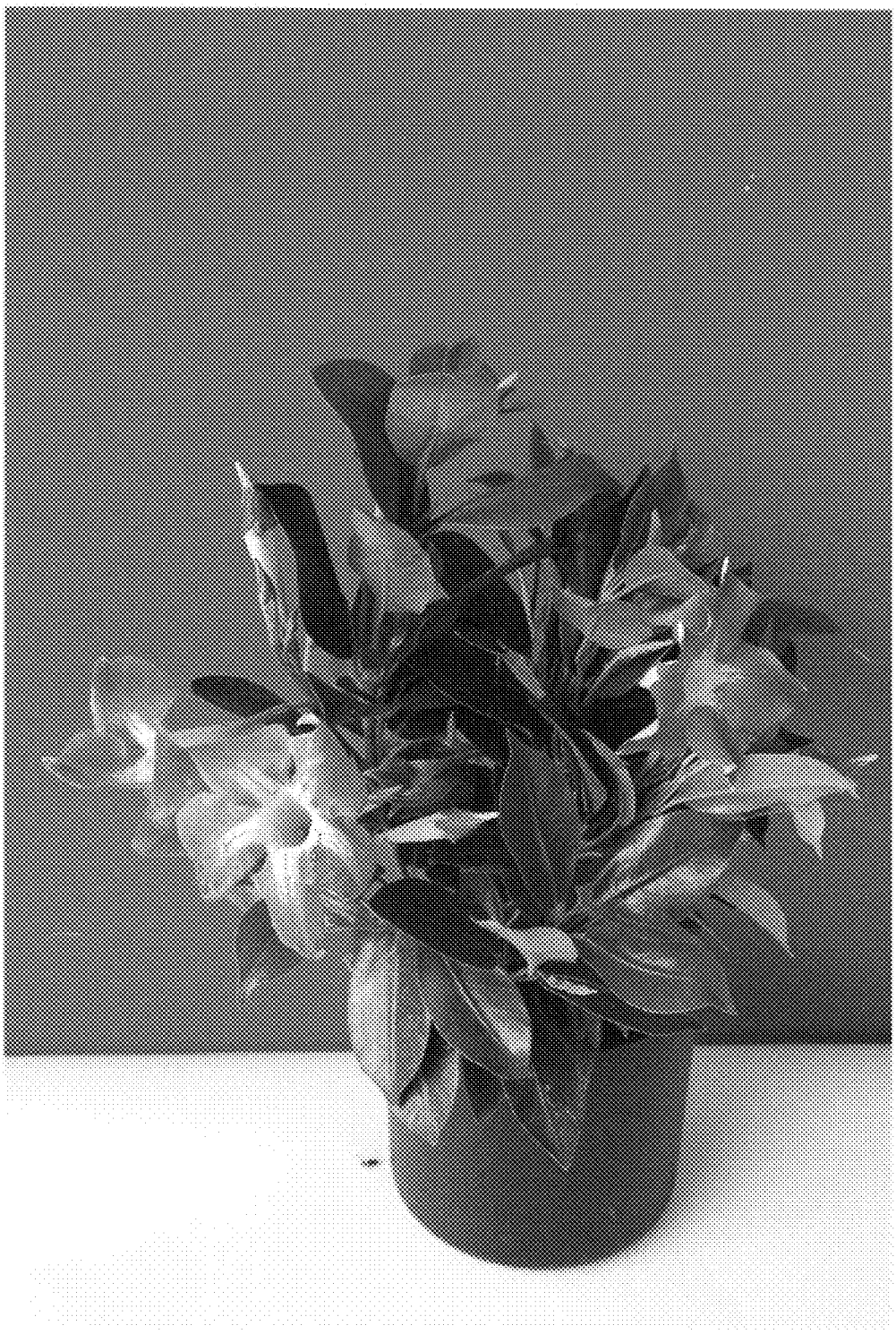

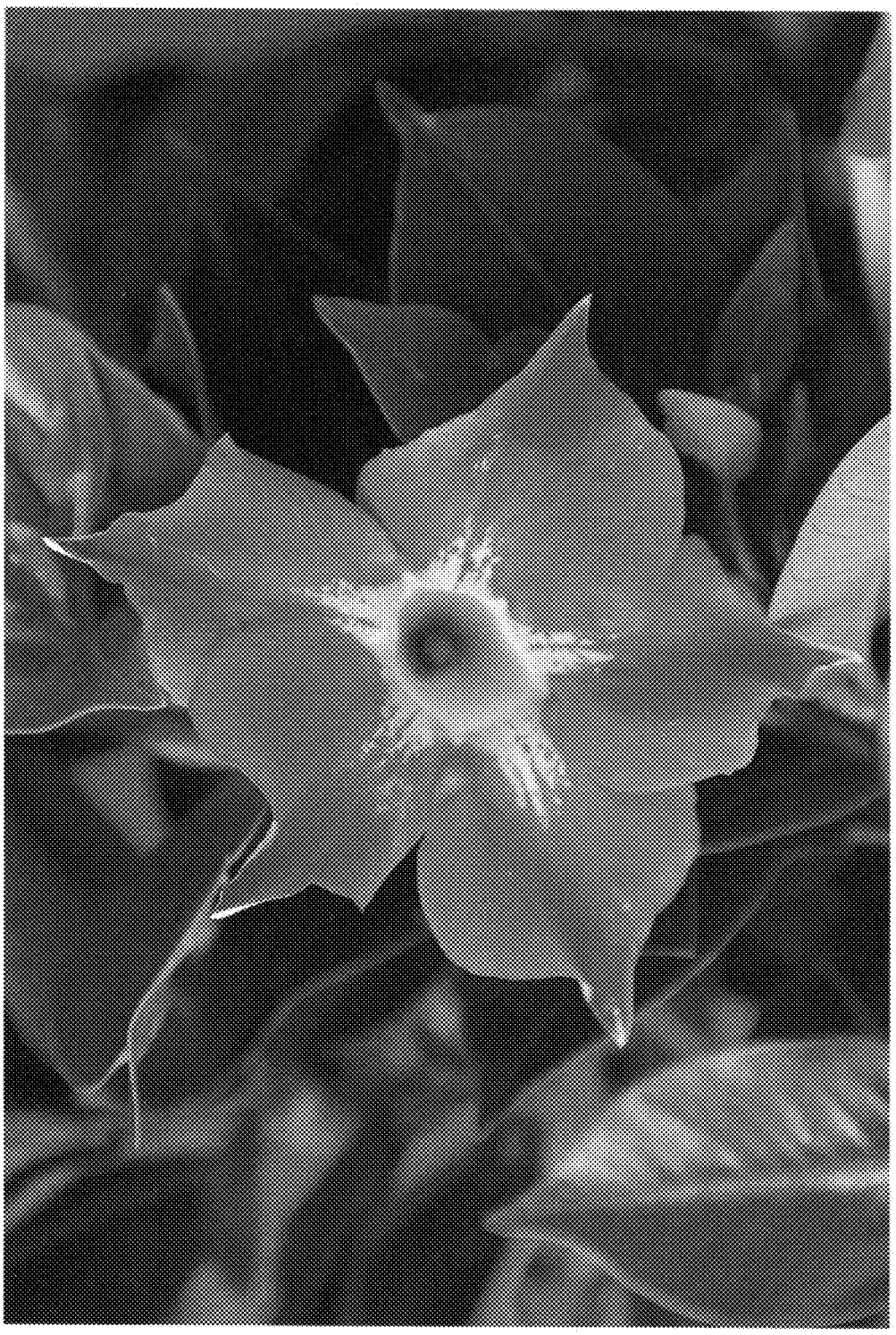

* * * * *